(12) United States Patent
DelloStritto et al.

(10) Patent No.: US 8,719,712 B2
(45) Date of Patent: May 6, 2014

(54) ADAPTIVE DISPLAY FOR PATIENT MONITORING

(75) Inventors: James J. DelloStritto, Jordan, NY (US); Navaneeth Ranganna, Syracuse, NY (US); Sumeet Dipak Mehta, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 723 days.

(21) Appl. No.: 12/907,882

(22) Filed: Oct. 19, 2010

(65) Prior Publication Data

US 2012/0096367 A1    Apr. 19, 2012

(51) Int. Cl.
*G06F 3/00* (2006.01)
*G06F 3/048* (2013.01)

(52) U.S. Cl.
USPC ............ 715/747; 715/782; 715/783; 715/788

(58) Field of Classification Search
USPC .......................................... 715/782, 783, 788
See application file for complete search history.

(56) References Cited

U.S. PATENT DOCUMENTS

| | | | |
|---|---|---|---|
| 7,293,040 B2 * | 11/2007 | Terada ................................. | 1/1 |
| 7,546,571 B2 * | 6/2009 | Mankin et al. ................ | 716/137 |
| RE43,082 E * | 1/2012 | Gutowitz ......................... | 341/22 |
| 8,499,252 B2 * | 7/2013 | Skidmore ...................... | 715/777 |
| 8,583,421 B2 * | 11/2013 | Slocum et al. ..................... | 704/9 |
| 2005/0188083 A1 * | 8/2005 | Biondi et al. ................. | 709/224 |
| 2006/0231108 A1 * | 10/2006 | Novatzky et al. ............. | 128/898 |
| 2007/0188495 A1 | 8/2007 | Kiani | |
| 2008/0288500 A1 * | 11/2008 | Sapounas ........................... | 707/9 |
| 2010/0050114 A1 * | 2/2010 | Braun et al. ................... | 715/788 |
| 2010/0238089 A1 | 9/2010 | Massand | |

OTHER PUBLICATIONS

International Search Report and Written Opinion in PCT/US2011/055716 mailed May 18, 2012, 9 pages.

* cited by examiner

*Primary Examiner* — David Phantana Angkool
(74) *Attorney, Agent, or Firm* — Merchant & Gould P.C.

(57) ABSTRACT

A system for displaying physiological parameters includes: a central processing unit (CPU) that is configured to control operation of a monitor device; a display screen; and a set of one or more computer readable data storage media storing software instructions that, when executed by the CPU, cause the monitor device to: detect a device that is added to the system, the device being used to measure at least one physiological parameter associated with a patient; provision the device; allow a user to select a skin defining a layout for displaying data associated with the physiological parameter measured by the device; allow the user to select a position of a window displaying the skin, the position selected from one of a plurality of cells on a matrix displayed on the display screen; and display the window on the display screen at the position.

18 Claims, 16 Drawing Sheets

ADAPTIVE DISPLAY FOR PATIENT MONITORING

BACKGROUND

Healthcare practitioners can be constrained by the inability of devices used to monitor and collect physiological data from patients to communicate with electronic health records, existing infrastructure, and other devices. The medical device research community has responded by creating next generation devices that are small, wireless, and wearable. New devices may incorporate a simple display, processor, and multitude of companion sensors. As "smart" monitoring tools penetrate healthcare markets, new ways are needed to assist the practitioners in visualizing the collected data.

SUMMARY

In one aspect, a system for displaying physiological parameters includes: a central processing unit (CPU) that is configured to control operation of a monitor device; a display screen; and a set of one or more computer readable data storage media storing software instructions that, when executed by the CPU, cause the monitor device to: detect a device that is added to the system, the device being used to measure at least one physiological parameter associated with a patient; provision the device; allow a user to select a skin defining a layout for displaying data associated with the physiological parameter measured by the device; allow the user to select a position of a window displaying the skin, the position selected from one of a plurality of cells on a matrix displayed on the display screen; and display the window on the display screen at the position.

In another aspect, a monitor device including a central processing unit (CPU) and at least one computer readable data storage medium storing software instructions that, when executed by the CPU, cause the monitor device to generate a user interface comprising: a matrix defined on a display of the monitor device, the matrix including a plurality of cells, each of the cells being configured to display a window displaying aspects of a physiological parameter measured by a sensor device associated with a patient, the matrix displaying at least two windows for two different patients; and a skin selection module displaying a plurality of skins, each of the skins defining a layout for displaying data associated with the physiological parameter measured by the sensor device.

In yet another aspect, a method for displaying physiological parameters includes: detecting a device that is added, the device being used to measure at least one physiological parameter associated with a patient; allowing a user to select a skin defining a layout for displaying data associated with the physiological parameter measured by the device; allowing the user to select a position of a window displaying the skin, the position selected from one of a plurality of cells on a matrix displayed on a display screen; and displaying the window on the display screen at the position.

DETAILED DESCRIPTION

The present disclosure relates to systems and methods that allow data from a plurality of devices to be collected and displayed. In some examples, devices that are used to collect the data are automatic detected and provisioned, and the display of the data can be customized.

One embodiment includes a computer platform including a display device which wirelessly communicates with body-worn sensors. The display device can be sited in a variety of physical locations, such as hospital nurse's station or practitioner's examination room. The device display is configured to create a customized visualization and record of information captured by the body-worn sensors, which wirelessly send physiological data to the display device.

In one embodiment, upon introduction of a new device, the user is prompted and provided with an interface that allows the user to choose what, where and how to display data. The resultant output of configuring the display is a digital skin. Multiple skins can be created and provided to users of the devices and systems. The platform can be tailored for use in full monitoring systems or in trending views for stored data in a database.

Figure 1:
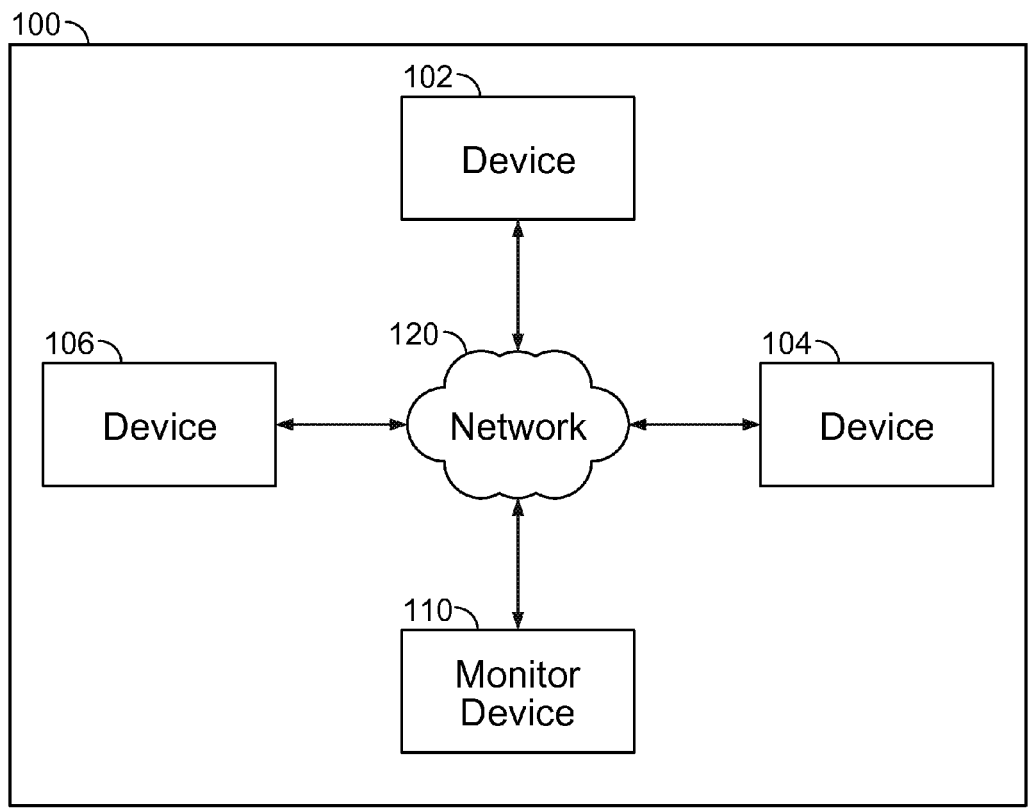
FIG. 1 shows an example system for collecting and displaying data associated with physiological parameters of patients.

FIG. 1 is a block diagram illustrating an example system 100 for collecting and displaying physiological data. As illustrated, the system 100 includes a network 120, a monitor device 110, and a plurality of devices 102, 104, 106.

The network 120 is an electronic communication network that facilitates communication between the devices 102, 104, 106 and the monitor device 110. The network 120 can include a set of computing devices and links between the computing devices. The computing devices in the network 120 use the links to enable communication among the computing devices in the network.

The network 120 can include routers, switches, mobile access points, bridges, hubs, intrusion detection devices, storage devices, standalone server devices, blade server devices, sensors, desktop computers, firewall devices, laptop computers, handheld computers, mobile telephones, and other types of computing devices. In various embodiments, the network 120 includes various types of links. For example, the network 120 can include wired and/or wireless links. The network 120 can be implemented as one or more local area networks (LANs), metropolitan area networks, subnets, wide area networks (such as the Internet), or can be implemented at another scale.

The monitor device 110 is a computing system that allows for storage, retrieval, manipulation, and display of data collected by one or more of the devices 102, 104, 106. As used herein, a computing system is a system of one or more computing devices. A computing device is a physical, tangible device that processes data. Example types of computing devices include personal computers, standalone server computers, blade server computers, mainframe computers, handheld computers, smart phones, special purpose computing devices, and other types of devices that process data.

The monitor device 110 can include at least one central processing unit ("CPU" or "processor"), a system memory, and a system bus that couples the system memory to the CPU. The system memory is one or more physical devices that can include a random access memory ("RAM") and a read-only memory ("ROM"). A basic input/output system containing the basic routines that help to transfer information between elements within the monitor device 110, such as during startup, is stored in the ROM. The monitor device 110 further includes a mass storage device. The mass storage device is able to store software instructions and data.

The mass storage device and its associated computer-readable data storage media provide non-volatile, non-transitory storage for the monitor device 110. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the monitor device 110 can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the monitor device 110.

As noted previously, the monitor device 110 can operate in a networked environment using logical connections to remote network devices through the network 120, such as a local network, the Internet, or another type of network. The monitor device 110 connects to the network 120 through a network interface unit connected to the bus. The network interface unit may also be utilized to connect to other types of networks and remote computing systems. The monitor device 110 also includes an input/output controller for receiving and processing input from a number of other devices, including a keyboard, a mouse, a touch user interface display screen, or another type of input device. Similarly, the input/output controller may provide output to a touch user interface display screen, a printer, or other type of output device.

As mentioned briefly above, the mass storage device and the RAM of the monitor device 110 can store software instructions and data. The software instructions include an operating system suitable for controlling the operation of the monitor device 110. The mass storage device and/or the RAM also store software instructions, that when executed by the CPU, cause the monitor device 110 to provide the functionality of the monitor device 110 discussed herein.

For example, the mass storage device and/or the RAM can store software instructions that, when executed by the CPU, cause the monitor device 110 to display user interface screens that display the data that is provided by the devices 102, 104, 106. In this example, the user interface can be configured by the user to display data from more than one of the devices 102, 104, 106, and the user interface can be modified to display data in different formats depending on the application and preferences of the user.

In this example, each of the devices 102, 104, 106 is a sensor device that collects data from one or more patients. Such data can include, without limitation, physiological data like temperature, heart rate, blood pressure, oxygen saturation, etc.

In some examples, each of the devices 102, 104, 106 is a computing device that is worn by the individual. Such devices typically include a system memory, a processing unit, a physiological sensor, a radio device, a housing, a printed circuit board, and a power source. Additional details regarding such example devices are described in U.S. patent application Ser. No. 12/827,817 filed on Jun. 30, 2010, the entirety of which is hereby incorporated by reference. Other devices can also be used to measure physiological data.

The devices 102, 104, 106 can also be one or more intermediary devices that receive data from one or more sensors, manipulate and/or store that data, and forward the data on to the monitor device 110. For example, the devices 102, 104, 106 can include one or more desktop, laptop, or wall-mounted devices.

Figure 2:
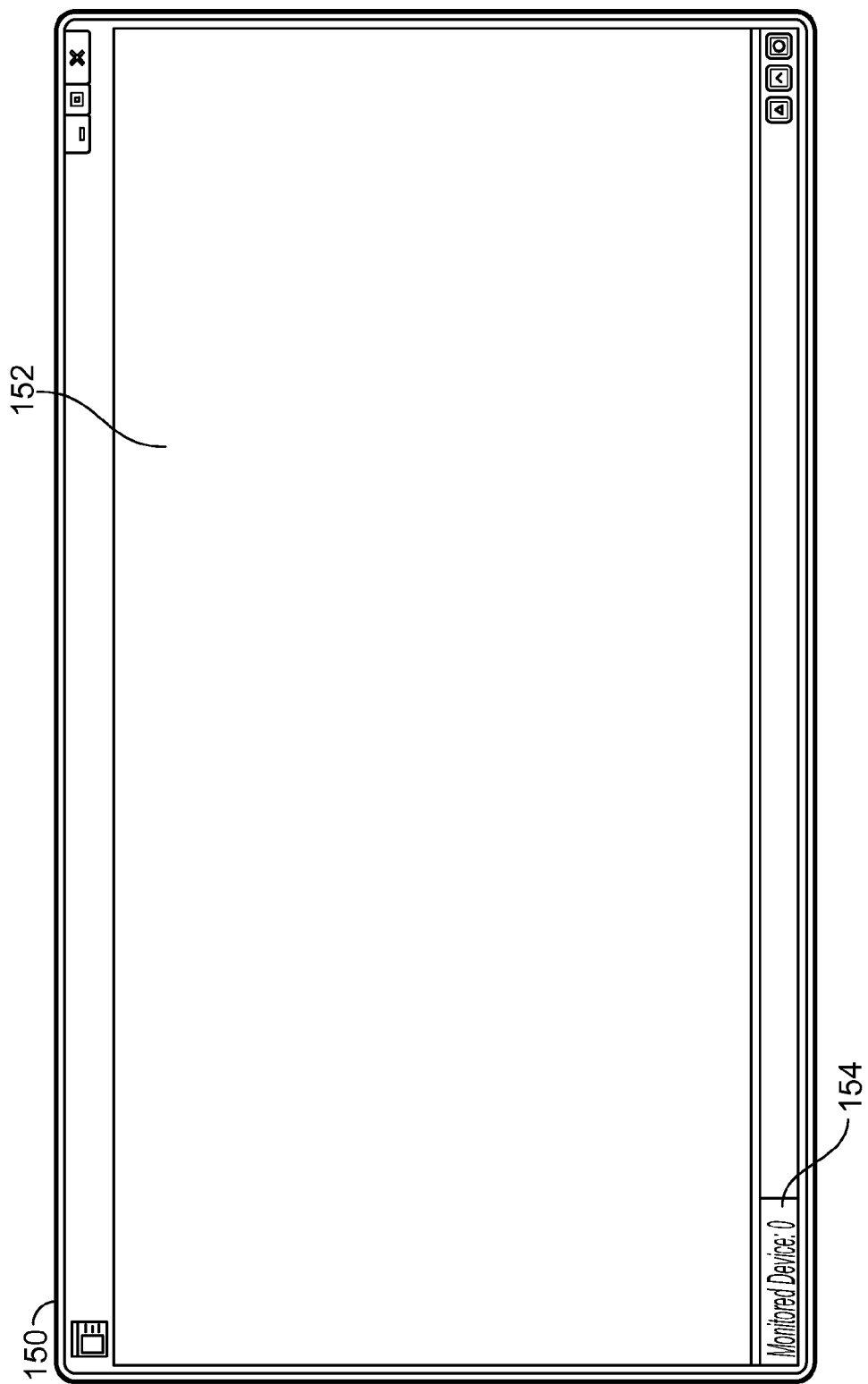
FIG. 2 shows an example user interface of a monitor device of the system of FIG. 1 for displaying the data.

Referring now to FIG. 2, an example user interface 150 of the monitor device 110 is shown. The interface 150 is typically displayed on a display screen such as a flat panel or CRT display.

The interface 150 includes a main screen region 152 in which data from the devices 102, 104, 106 is shown. As illustrated, none of the devices 102, 104, 106 is connected to the monitor device 110, so no information is displayed in the main screen region 152.

A status box 154 of the interface 150 indicates the number of devices that are currently connected to the monitor device 110. Since no devices are currently connected, the status box 154 indicates: "Monitored Devices: 0." As devices connect to the monitor device 110, the status box 154 is updated to indicate the number of connected devices.

Figure 3:
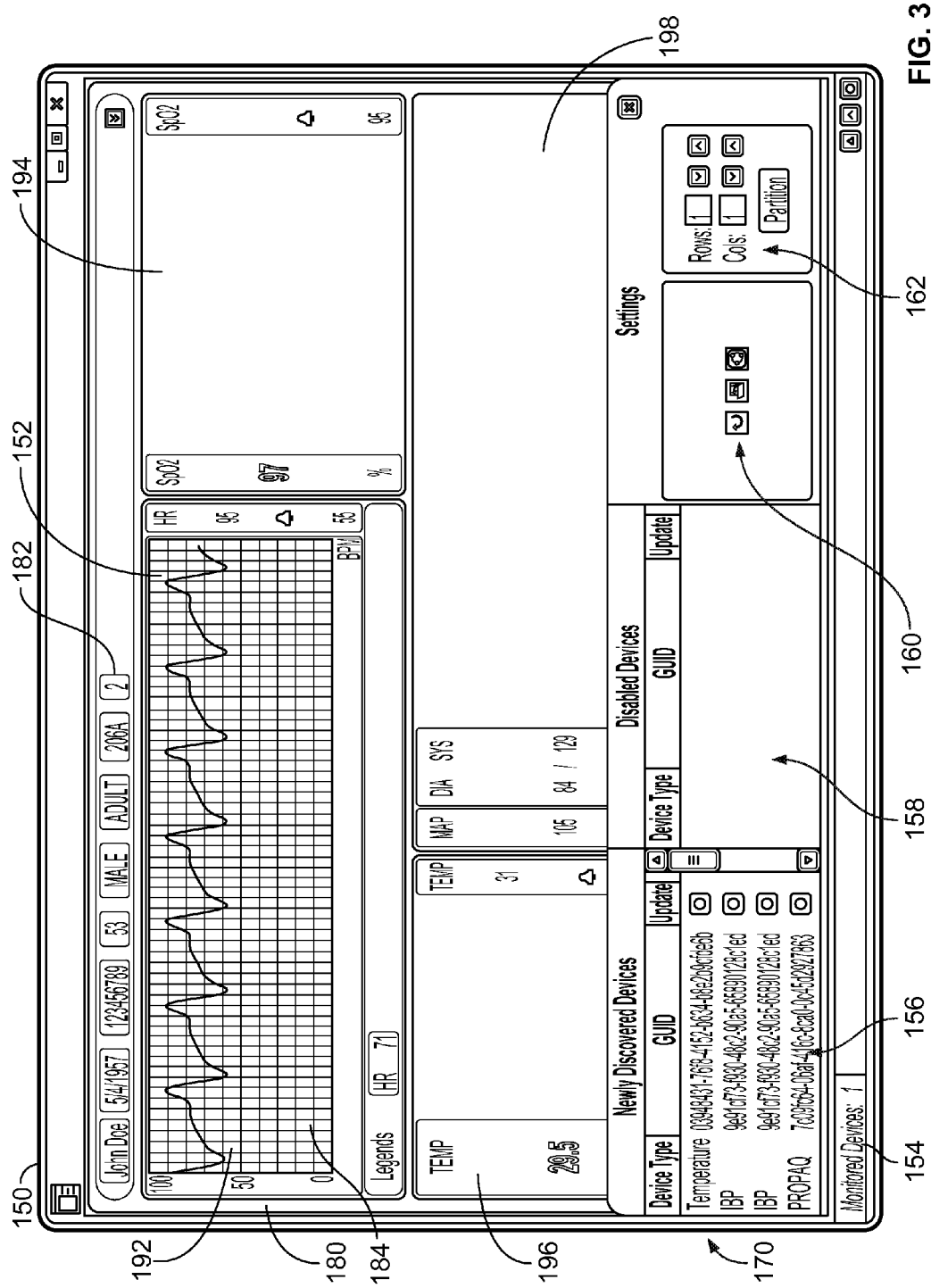
FIG. 3 shows another view of the user interface of FIG. 2.

Referring now to FIG. 3, the interface 150 is shown with the monitor device connected to one of the devices 102, 104, 106. The status box 154 indicates that "1" device is being monitored.

Since only one device is connected, the main screen region 152 displays a single window 180 associated with the device. The window 180 generally includes a device status area 182 and a content area 184.

The device status area 182 contains data regarding the status of the connected device 102, 104, 106. Status information can include, without limitation, information about the patient to which the device is connected (e.g., name, date of birth, identification number, age, sex, etc.) and location (e.g., "206A" represents a room located on the second floor of the building). Other information can also be provided.

The content area 184 is broken into one or more parameter reporting frames. Each of the parameter reporting frames contains a representation of a different physiological parameter of a patient. The representations are based on one or more measurements of the physiological parameters of a monitored patient. In addition, each of the parameter reporting frames contains an alarm reporting area.

The content area 184 can also be used to report alarms specified by upper alarm limits and lower alarm limits for the physiological parameters. The upper alarm limits and the lower alarm limits define the alarm ranges for the physiological parameters. Alarms associated with the physiological parameters are active when measurements of the physiological parameters are outside the alarm range for the physiological parameters.

In the example shown, the content area 184 contains an electrocardiograph frame 192, an SpO2 frame 194, a temperature frame 196, and non-invasive blood pressure frame 198. Other parameters and configurations are possible.

Additional details regarding such windows can be found in U.S. patent application Ser. No. 12/751,579 filed on Mar. 31, 2010, the entirety of which is hereby incorporated by reference.

In addition, the interface 150 includes a command region 170 with a plurality of modules that provide additional information about the status of the interface and the devices connected thereto.

A connection window 156 lists each device that is connected to the monitor device 110 or within range of the monitor device 110. Information that is provided above each of the devices is the device type column (e.g., "PROPAQ"), a globally unique identifier ("GUID") column, and an update status column.

Devices that are already connected to the monitor device 110 are indicated with a green shield in the update status column. To load a connected device, the user can simply drag and drop the listed device directly from the connection window 156 to the main screen region 152 at the desired position, as described below.

If a particular device does not have a device data sheet or any skins to view the device (as described further below), the shield associated with the update status for the device is red to signify that the device cannot be loaded on the screen.

When a device is encountered, the monitor device 110 will automatically prompt the user to download the device data sheet and at least one default skin that was generated by the manufacturer.

The device data sheet is a modeling mechanism through which any device used to gather physiological data, such as different sensors, can be modeled. The model is turned into a communicable data dictionary that can be deciphered by any other machines supporting an interpreter of the data dictionary, thereby enabling information interoperability. Additional details regarding such device data sheets can be found in U.S. patent application Ser. No. 11/905,811 filed on Oct. 4, 2007 and U.S. patent application Ser. No. 11/905,829 filed on Oct. 4, 2007, the entireties of which are hereby incorporated by reference.

As described further below, the skin defines how data from the devices are displayed on the monitor device 110. The user can manipulate or choose different skins to define how the data is displayed.

A disabled window 158 of the command region 170 lists devices that are still connected to the monitor device 110 but that are not displayed on the main screen region 152. Information provided about each of the disabled devices includes device type, GUID, and update status. A device can be disabled by selecting a disable item in a menu associated with the device, as described further below.

A settings window 160 of the command region 170 allows various configurations for the monitor device 110 to be set. Specifically, a refresh button allows the user to apply a skin of a currently-selected device to all other devices of a similar type shown on the main screen region 152. A download button allows the user to launch an application, such as a browser, to view an external site to obtain additional skins to be used with the devices. A ports button allows a ports configuration to be accessed to provision devices that are hard wired to the monitor device 110.

A grid window 162 of the command region 170 defines the layout of the main screen region 152. Data from a plurality of devices (e.g., the devices 102, 104, 106) can be shown at the same time on the main screen region 152. The devices 102, 104, 106 can be from a single patient. Alternatively, the device 102, 104, 106 can be from multiple patients. Therefore, the grid window 162 allows for flexibility so that multiple sensor data can be shown from a single patient or multiple patients.

To accommodate the difference devices, the main screen region 152 can be divided into a matrix including a plurality of rows and/or columns. The grid window 162 allows the user to specify the configuration of the main screen region 152. The user can define the number of "Rows" and "Columns" for the main screen region 152 and select the "Partition" button to divide the main screen region 152 as desired. In this example, a single row and column are used, since data from a single device is shown. As the number of rows and columns is increased, data from multiple devices can be shown. See, e.g., FIGS. 6, 8, 9. Additional columns and rows can be added "on-the fly" so that data from additional devices can be shown.

Figure 4:
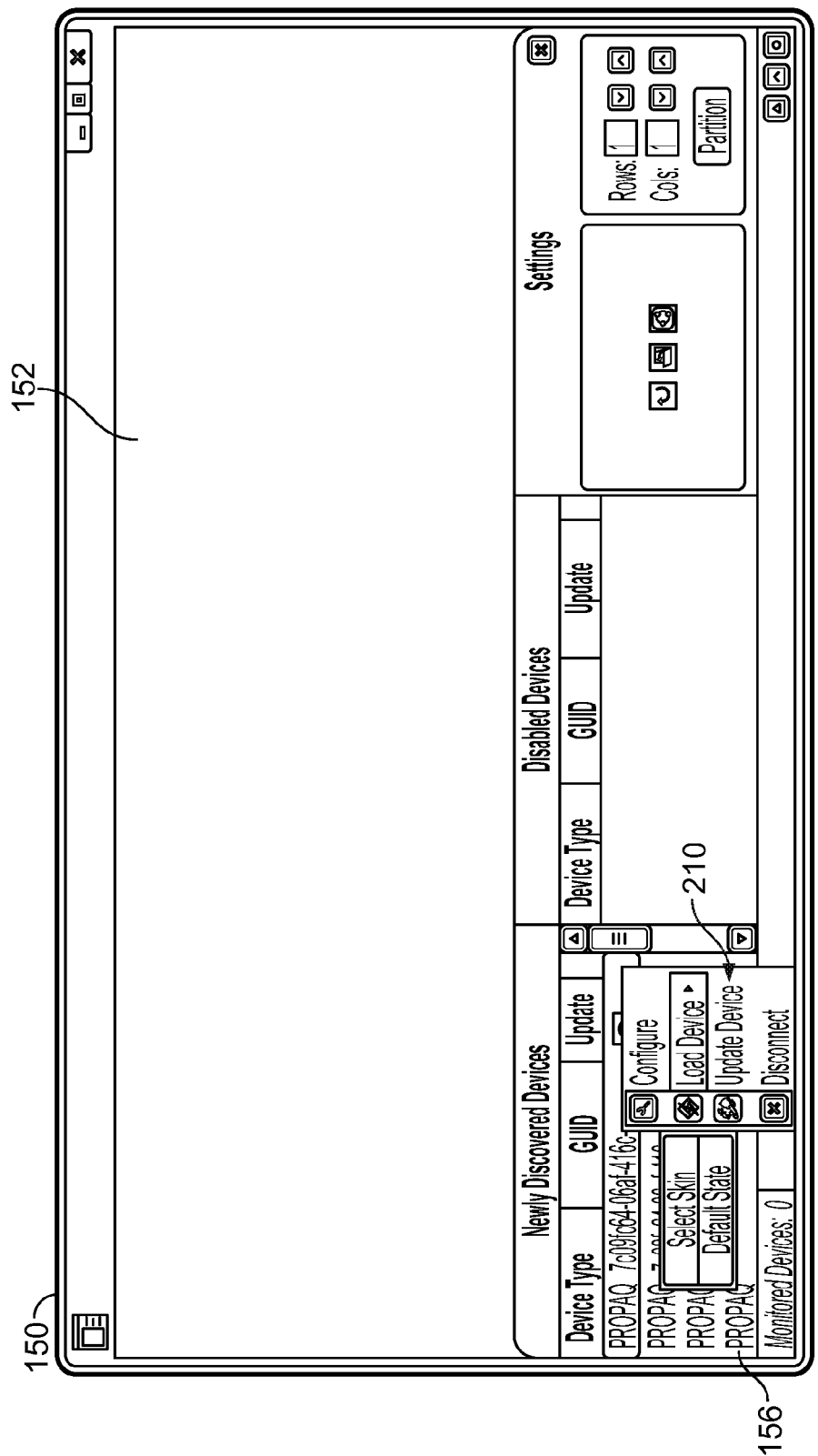
FIG. 4 shows another view of the user interface of FIG. 2.

Referring now to FIG. 4, when a new device does connect to the monitor device 110, a notification is provided that a new device has been discovered.

If the newly discovered device is of a known device type, the monitor device 110 will connect to a server using a protocol such as Welch Allyn Communications Protocol (WACP). WACP uses a taxonomy as a mechanism to define information and messaging. Taxonomy can be defined as description, identification, and classification of a semantic model. Taxonomy as applied to a classification scheme may be extensible. Semantic class-based modeling utilizing taxonomy can minimize the complexity of data description management by limiting, categorizing, and logically grouping information management and operational functions into families that contain both static and dynamic elements.

The server will provide device data sheets for the device and at least one basic skin to view the device. When a device, such as the device 102, connects, the monitor device 110 checks a look-up table to determine if the device 102 has previously connected. If so, the monitor device 110 determines if any updates are available.

By selecting one of the devices listed in the connection window 156, a menu 210 is provided that allows the user to perform various actions associated with the device, as described below.

If the user selects the "Configure" item from the menu 210, a wizard is generated that allows the user to create or modify an existing skin for the selected device. See FIGS. 10-13.

If the user selects the "Load Device" item, the user is prompted to select a desired skin or a default appearance that is used to display the information associated with the device. See FIG. 5.

If the user selects the "Update Device" item, the device data sheet or skins that are available for the device are updated. This can be used, for example, to obtain device data sheets and skins for devices that have red shields associated with them.

If the user selects the "Disconnect" item, the selected device is disconnected from the monitor device 110.

Figure 5:
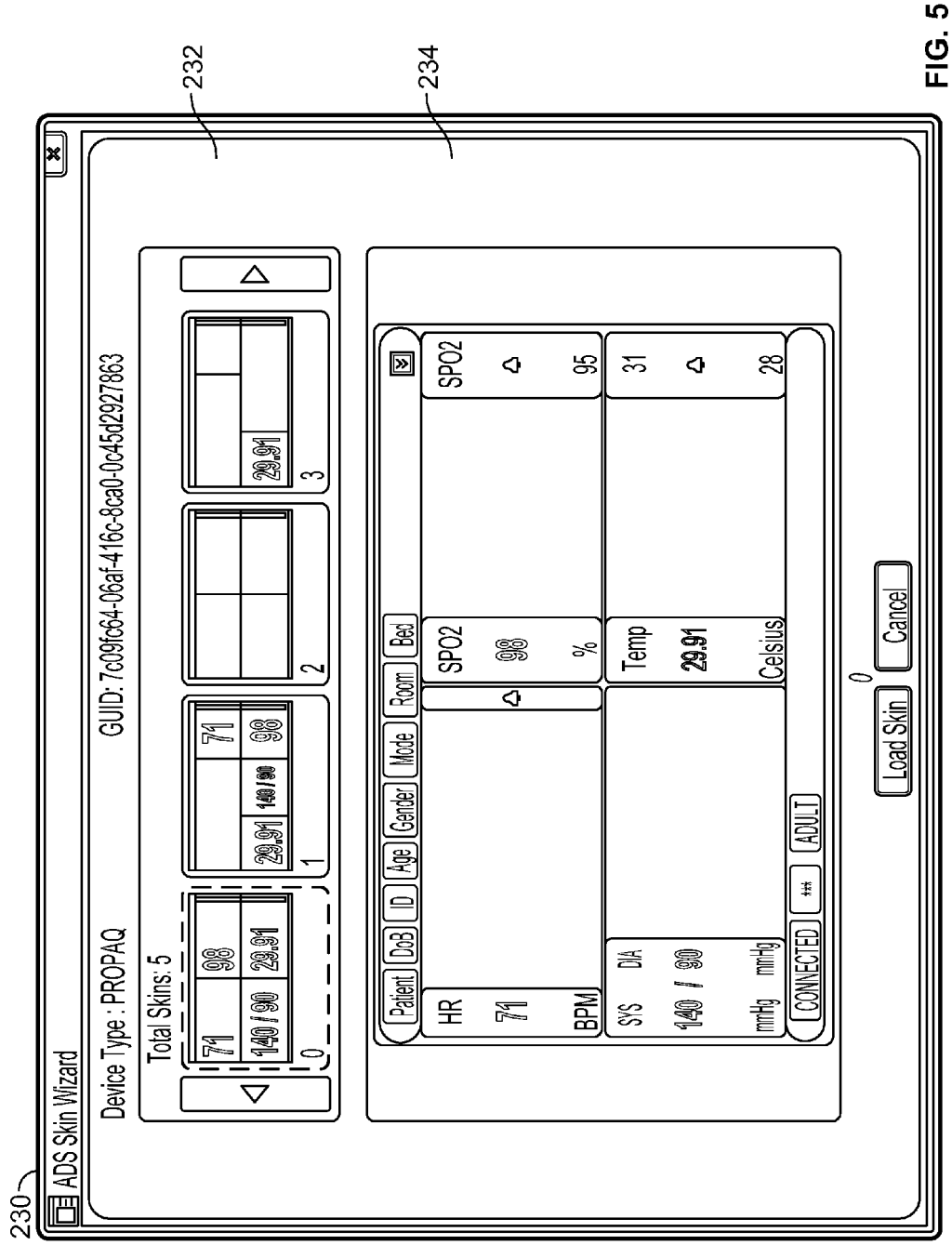
FIG. 5 shows an example user interface of the monitor device of the system of FIG. 1 for selecting a skin.

Referring now to FIG. 5, when the user chooses to load a device using the menu 210, an interface 230 loads that allows the user can select a desired skin for the device from a plurality of different skins associated with the device. As described previously, each skin defines a different layout for displaying the data associated with the device. For example, the highlighted skin "0" includes a two by two matrix of the same size frames, while the skin "1" includes a two by three matrix having different sized frames.

In this example, the interface 230 includes a skin chooser region 232 that allows the user to cycle through all of the skins available for the particular device. Arrows allow the user to scroll right and left, and the selected skin is highlighted.

A preview of the selected skin is shown in a skin preview region 234 of the interface 230. The skin previous region 234 provides a representation of how the device data will be displayed on the main screen region 152 if the particular skin is chosen. When the desired skin is found, the user can select the "Load Skin" button on the skin preview region 234 to load the desired skin for the device.

Figure 6:
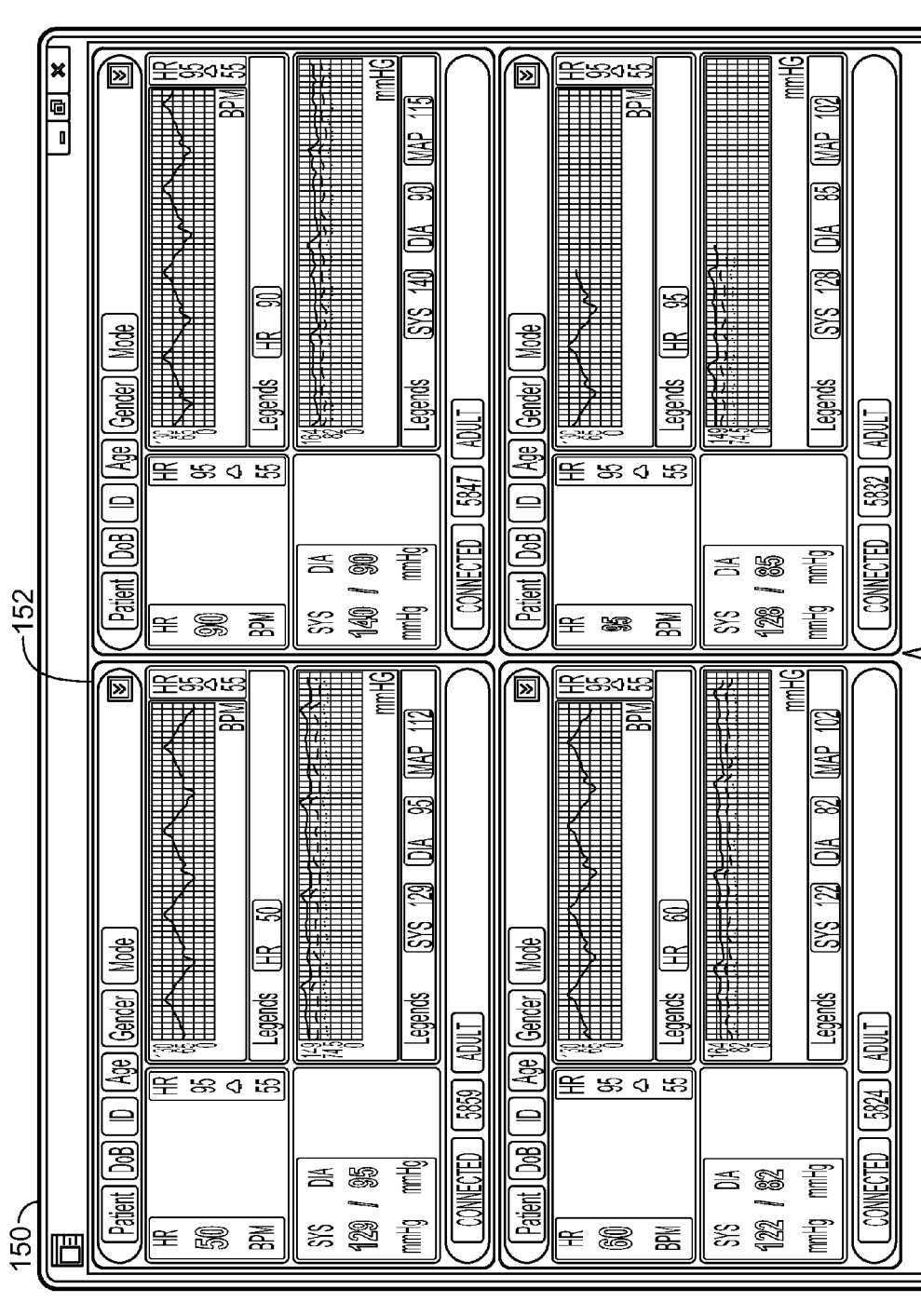
FIG. 6 shows another view of the user interface of FIG. 2.
Figure 6:
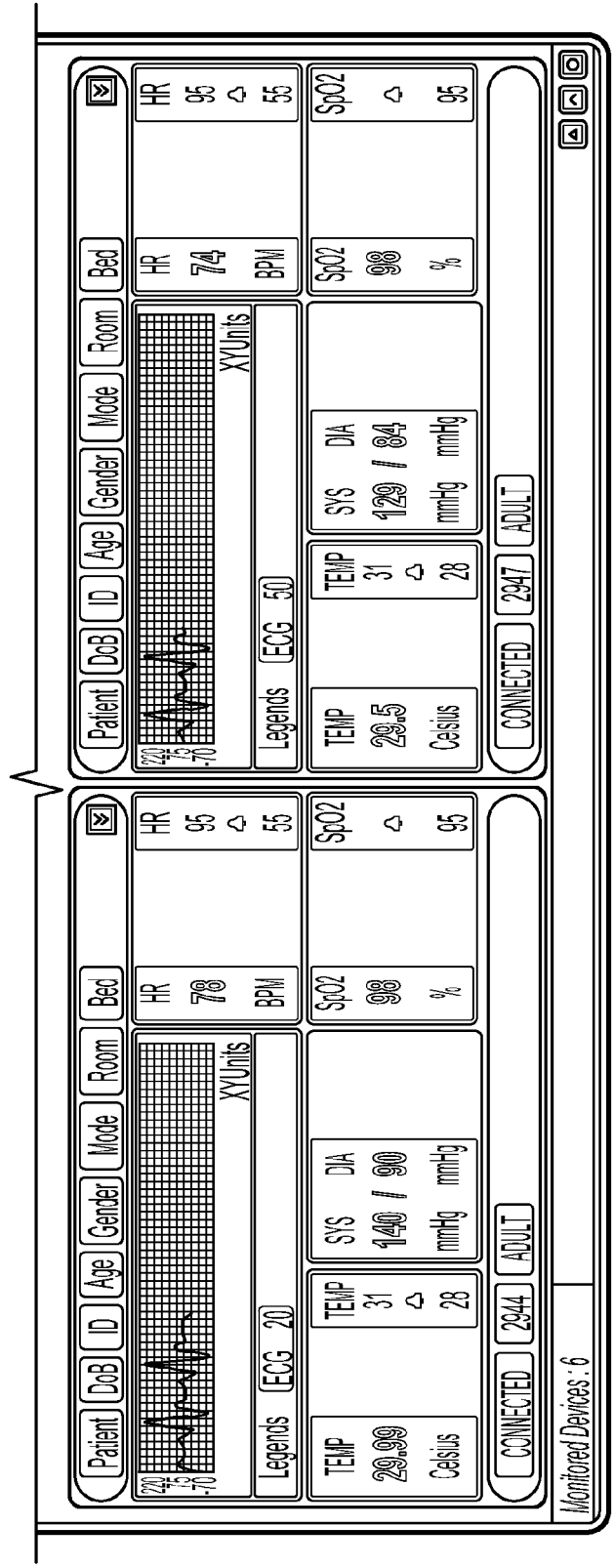

Referring now to FIG. 6, the main screen region 152 is shown divided into a three by two matrix to handle six devices. There are two different device types shown with different skins used to show the data from the different device types. The skins can be modified or new skins created to illustrate the data in a different way or to homogenous the views across the device types, if desired.

Figure 7:
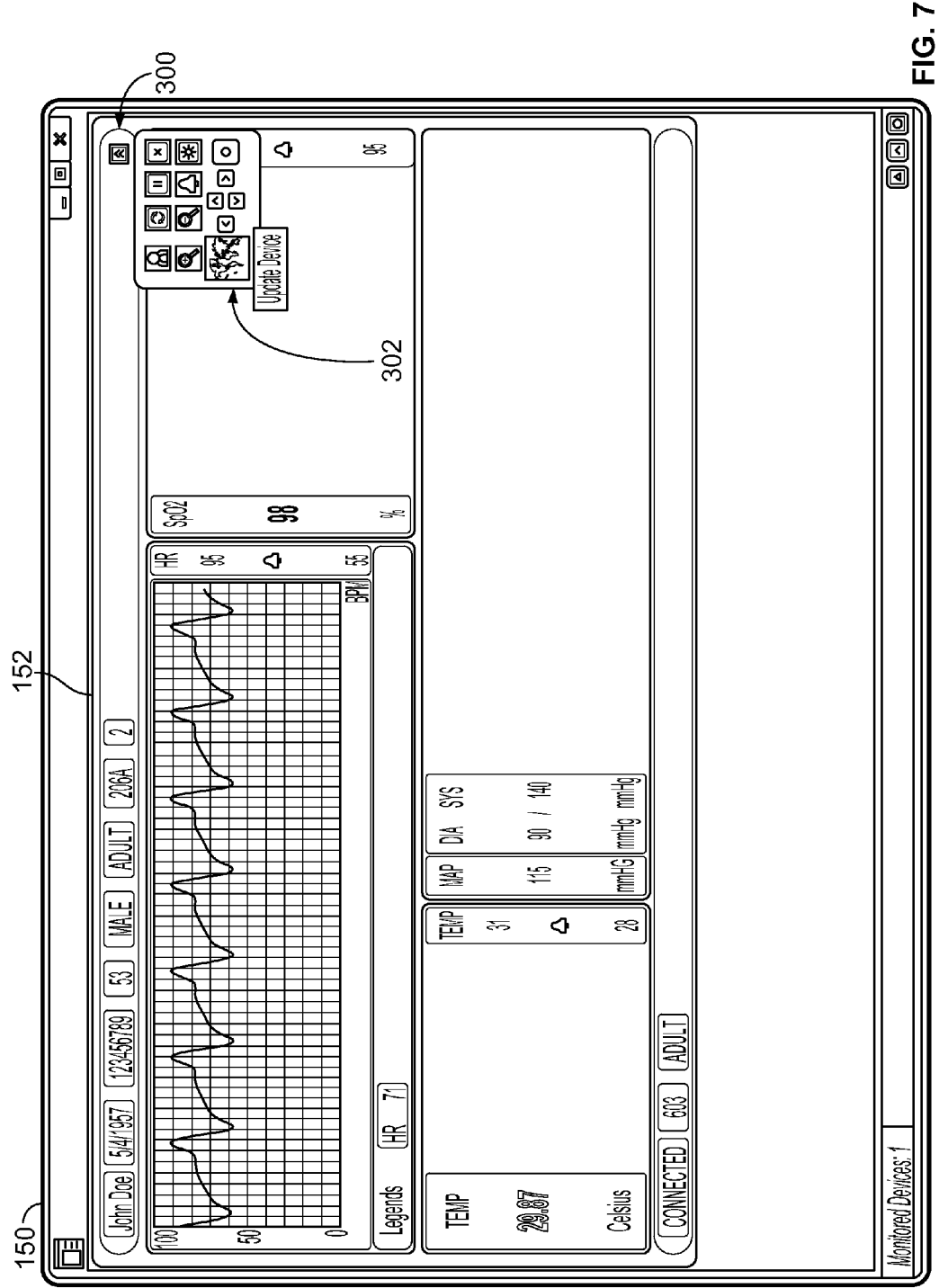
FIG. 7 shows another view of the user interface of FIG. 2.

Referring now to FIG. 7, the window for each of the devices shown on the main screen region 152 includes a control button 300. Once selected, the control button 300 provides access to a menu 302 that allows the user to perform various actions associated with the window for the selected device. These actions include the following:
- get patient icon—calls the device to get the current patient info;
- reconfigure—launches the interface 230—see FIG. 5;
- disable—removes the device view and sends it to the disabled window 158 of the command region 170—see FIG. 3;
- disconnect—disconnects the device and removes it from the screen;
- zoom in—launches a new larger zoomed window;
- zoom out—close a larger zoomed window and return to the main screen region 152;
- mute—mutes audible alerts;
- disables visual (border will flash when any one parameter is in an alert state) and audible alarms;
- update device—start the update service checking servers for device updates;
- merge—the four directional arrows allow a device view to merge cells to the left, right, up or down—see FIG. 8; and
- return the view back to the origin cell the device started in.

Figure 8:
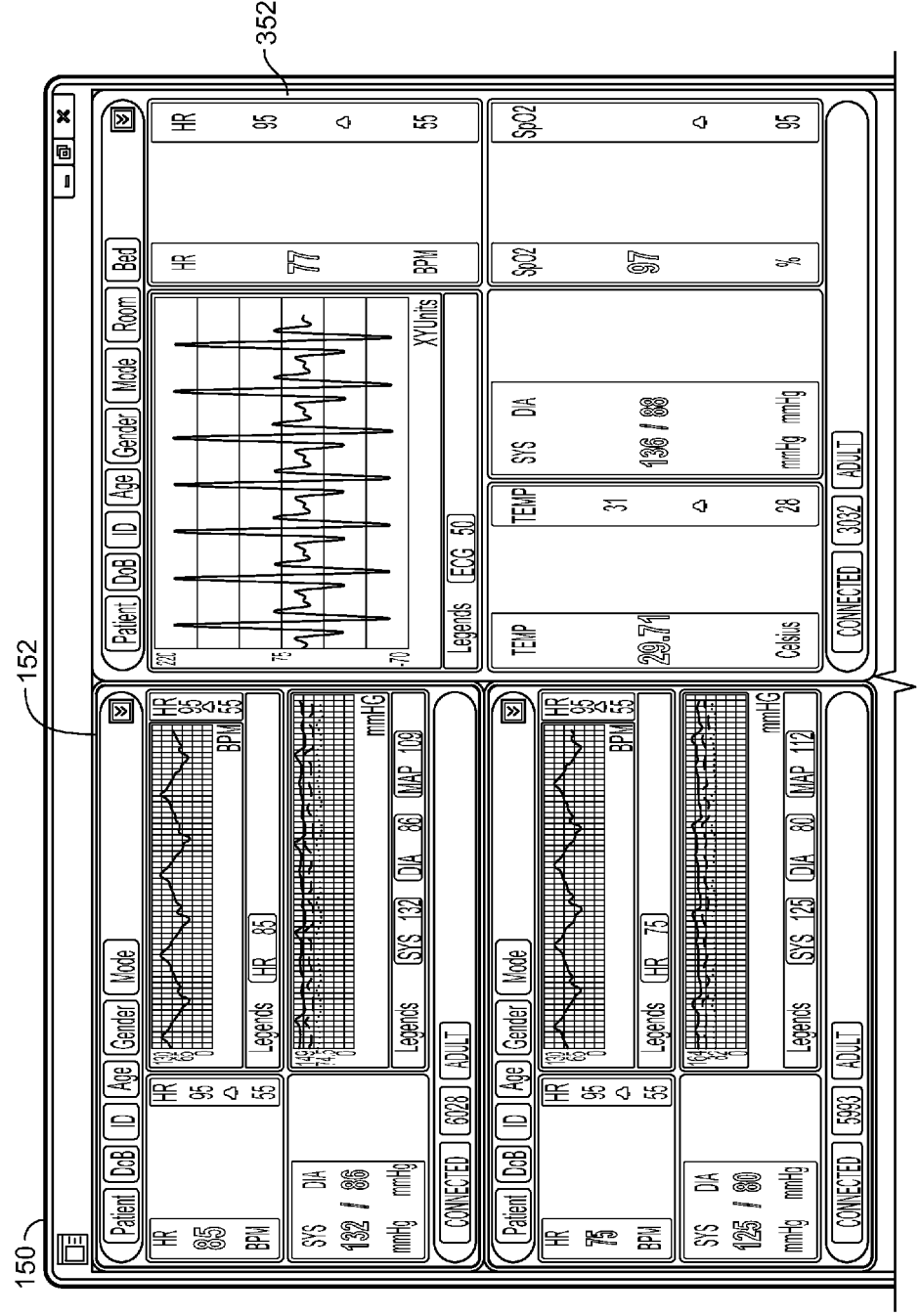
FIG. 8 shows another view of the user interface of FIG. 2.
Figure 8:
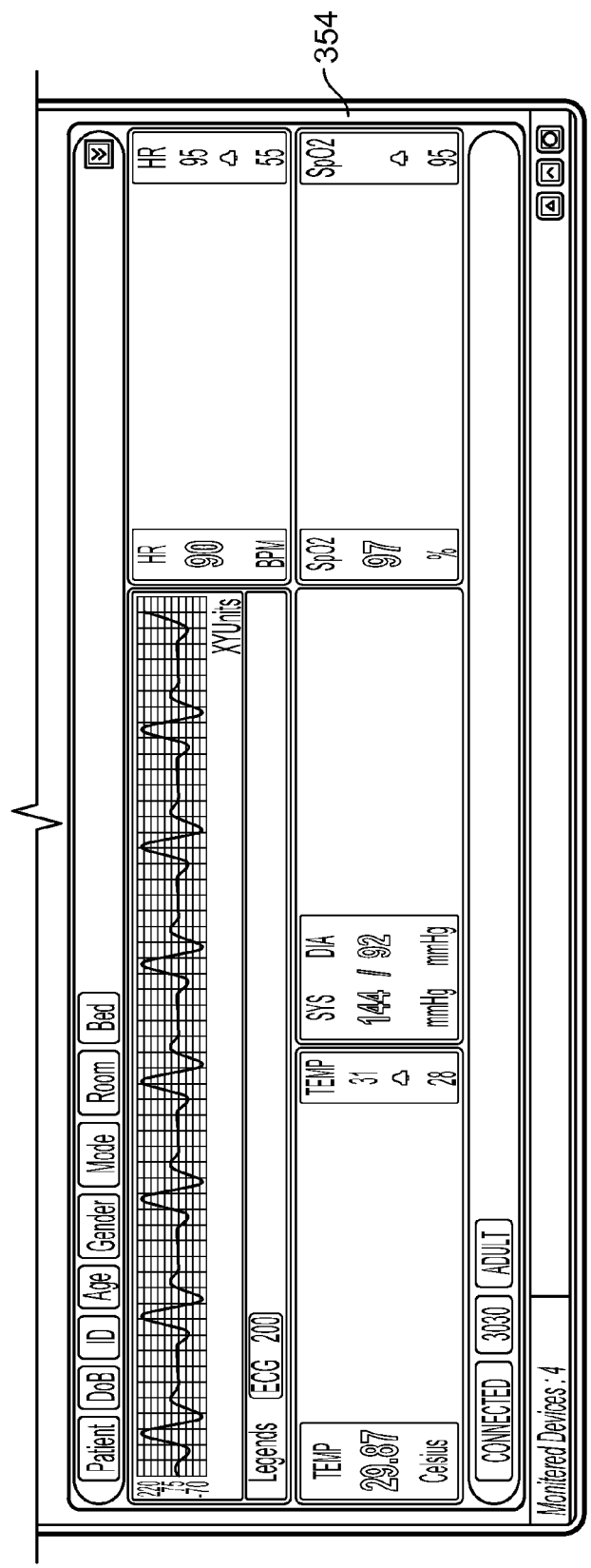

Referring now to FIG. 8, the merge item on the menu 302 (see FIG. 7) allows cells in the matrix of the main screen region 152 to be merged for larger display spaces. This is accomplished by selecting one cell, and then selecting a cell surrounding the selected cell (up, down, left, right) with which to merge.

For example, cells for the window 352 for one device have been merged so that the window 352 occupies a one by two enhanced cell. Similarly, cells for a window 354 for another device are merged so that the window 354 occupies a two by one enhanced cell. Such a configuration can be advantageous, for example, for viewing trends that extend horizontally along a time-based axis. The sizes and shapes for the windows can be further merged (e.g., increased and decreased in size) as desired by the user. Other configurations are possible.

Figure 9:
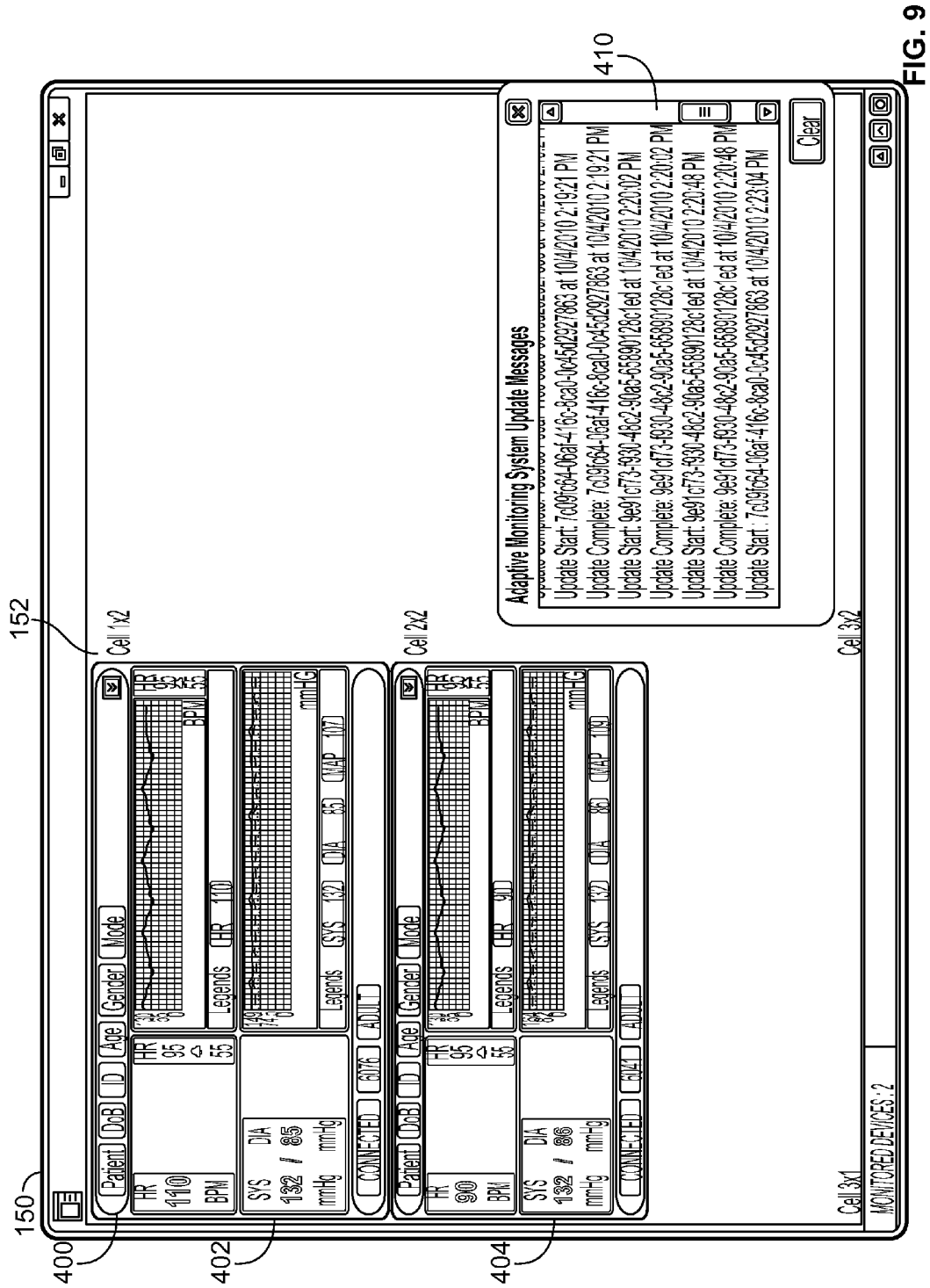
FIG. 9 shows another view of the user interface of FIG. 2.

Referring now to FIG. 9, the main screen region 152 is shown in a three by three matrix configuration. Two device windows 402, 404 for two devices are shown positioned in two of the cells of the main screen region 152. Additional device views can be dragged and dropped directly in the view by clicking and holding the window menu/title bar 400 of either of the device windows 402, 404. Using this method, the two device windows 402, 404 can be dragged and dropped to any of the remaining four empty cells in the main screen region 152. One or both of the device windows 402, 404 could also be merged to fill two or more empty windows. Further, additional devices listed in the connection window 156 (see FIG. 3) can be dragged and dropped at the desired position in the matrix to add the windows associated with the devices to the main screen region 152.

In addition, a messages window 410 provides a list of system level messages that may be important to the user. For example, messages regarding updates that are completed for each device, as well as device connects and disconnects, can be displayed.

Referring now to FIGS. 10-13, an example interface 500 for defining a skin for a window for a device is shown.

Figure 10:
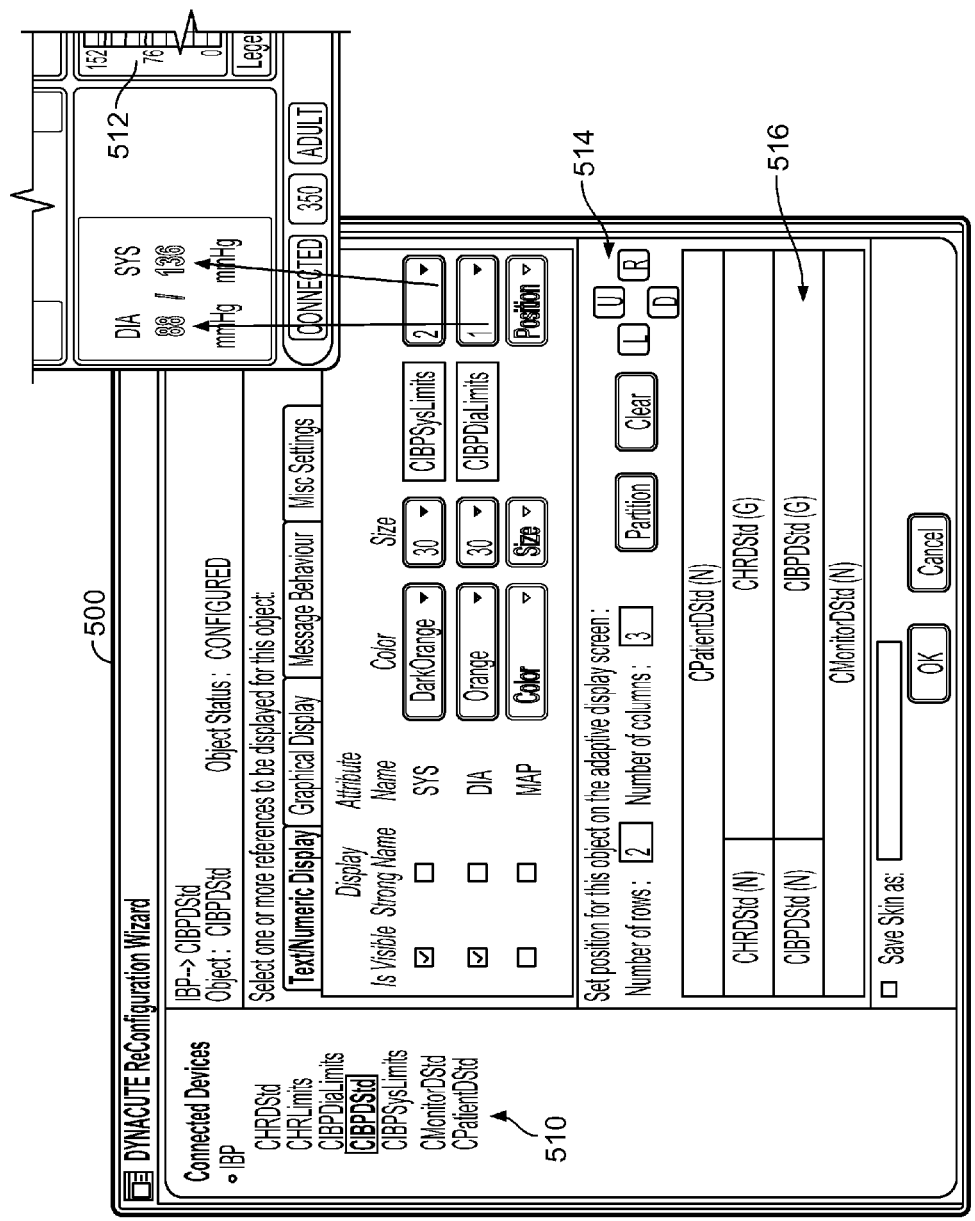
FIG. 10 shows an example user interface for creating a skin.

In FIG. 10, the textual and numerical display options for the skin are provided when the "Text/Numeric Display" tab is selected. An object window 510 lists the objects that are associated with the particular device. These objects are defined by the device data sheet for the device and represent the parameters that are sent by the device to the monitor device 110 using the WACP protocol. For example, the object selected, "CIBPDStd" is related to an invasive blood pressure reading.

Once an object is selected in the object window 510, the parameters on how the object is displayed are defined. Checking or unchecking the "Is Visible" checkbox for each parameter will show or hide the item. The "Strong Name" checkbox will define whether or not a text representation of the parameter is shown, such as "SYS" for systolic. Color and font sizes are also defined for the text. The position dropboxes are used when an object has multiple numerics to display. The ordering is determined by the position. An example snippet 512 of the main screen region shows this behavior.

A section 514 is used to layout and partition the screen. The number of rows and columns for the window are defined, and the "Partition" button will create the requested matrix below on a section 516. The 'U', 'D', 'L', 'R' arrow buttons are used to merge cells for customizing numeric and graphical displays. The "Clear" button will entirely reset the screen.

The section 516 defines how the objects are laid out in this grid. The "N" and "G" designations represent a numeric or graph type. Selecting the object in the object window 510 will allow the user to place the object on the grid. Selecting either numeric display or graphic display when placing the object will determine whether a graphic component or numeric component will be placed.

When the skin is complete, the user can name and save the skin for the particular device.

Figure 11:
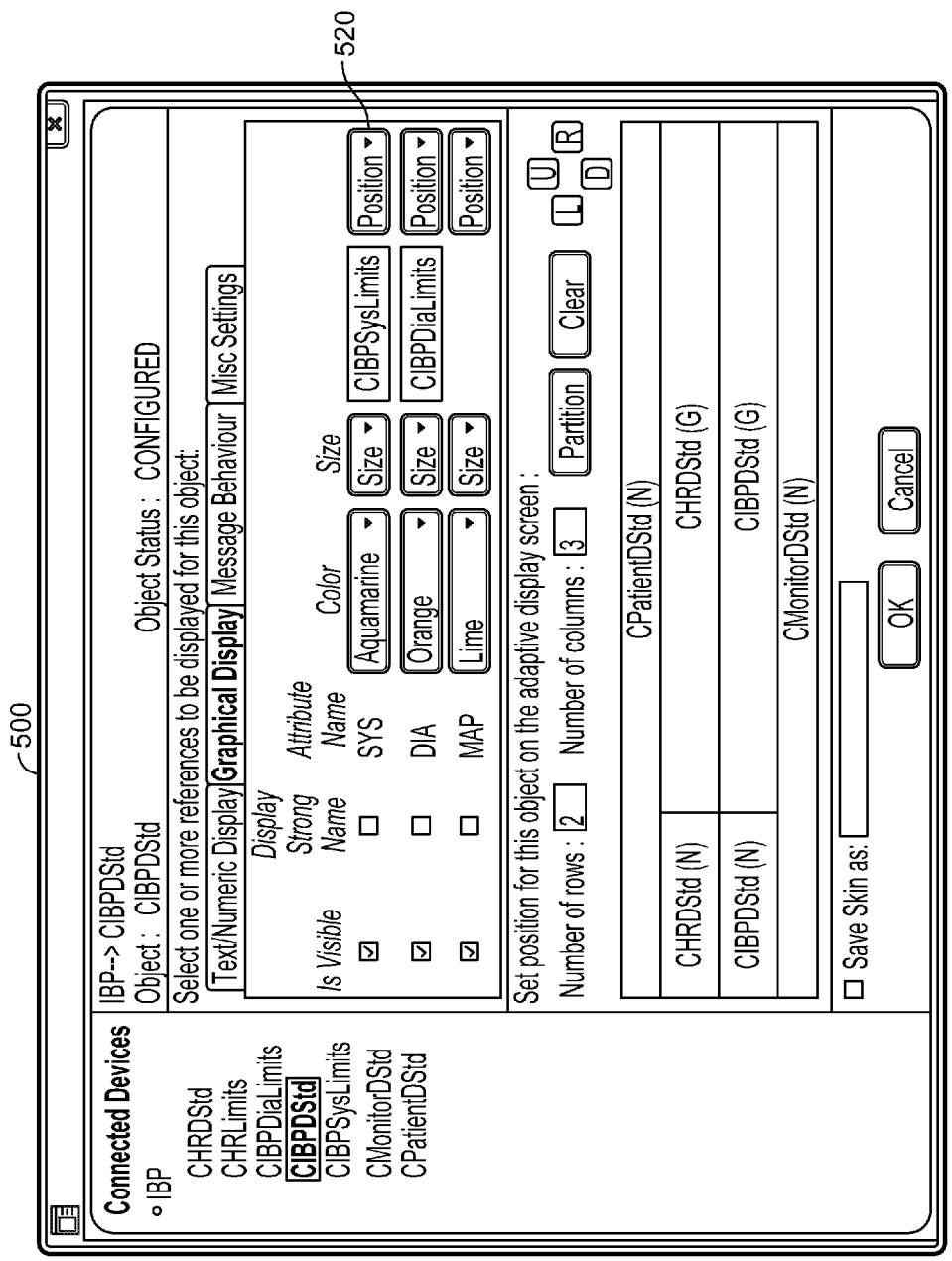
FIG. 11 shows another view of the user interface of FIG. 10.

In FIG. 11, the graphical display options for the skin are provided when the "Graphical Display" tab is selected. The graphic options are very similar to the numeric, except the parameter is illustrated as a graph instead of a numeric number. A legend on the bottom of a graph is generated by the position order of the specific parameter. The position can be defined using the dropdowns 520, and the legend is modified to reflect the positional order of the parameters.

Figure 12:
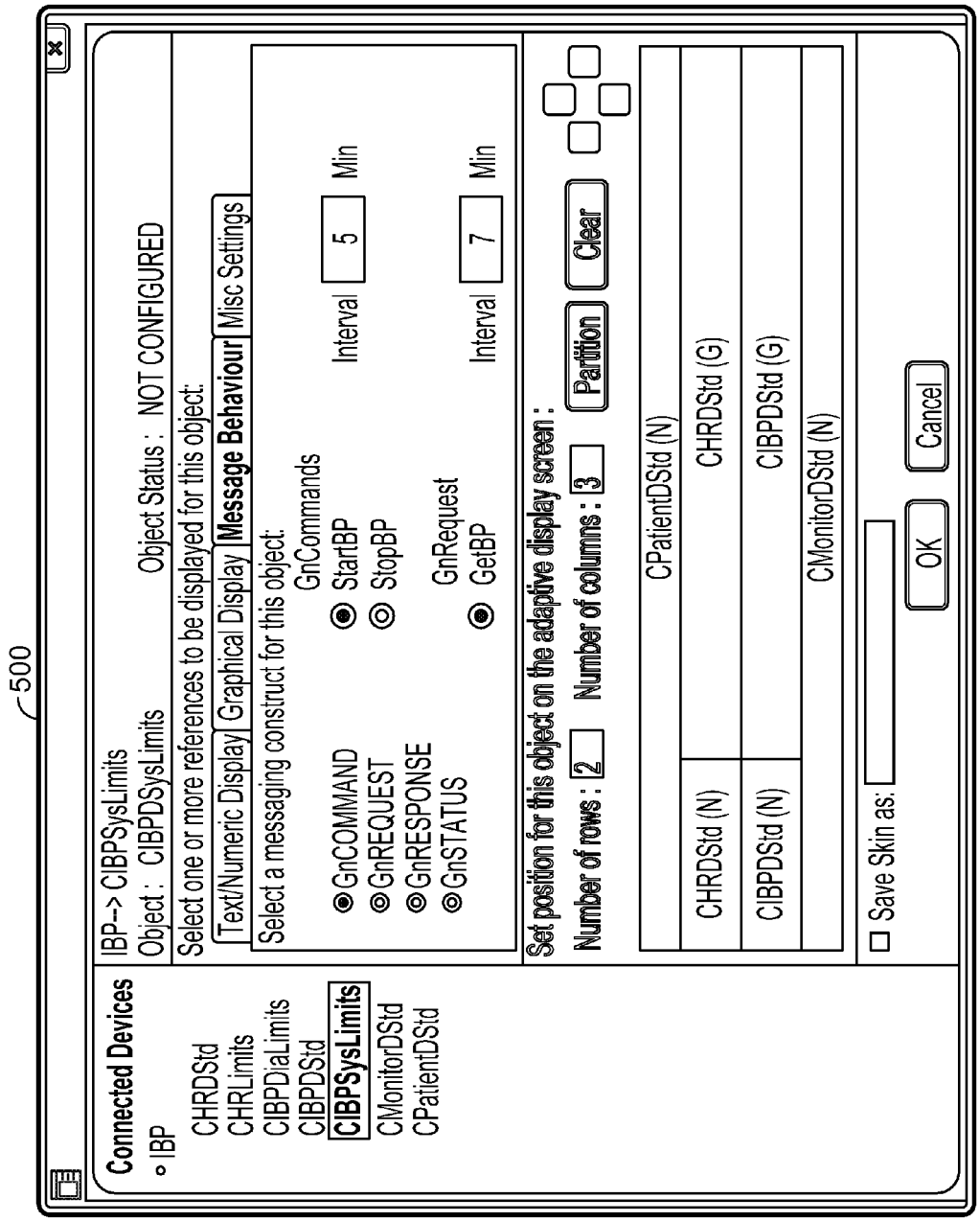
FIG. 12 shows another view of the user interface of FIG. 10.

In FIG. 12, the messaging behavior options between the devices 102, 104, 106 and the monitor device 110 are provided when the "Message Behavior" tab is selected. The messaging section allows the user to define a sequence of messages to be specified for interaction between the monitor device 110 and different types of devices like devices 102, 104, 106. The sequence of messages can allow the monitor device 110 to manipulate and control the devices 102, 104, 106 and to obtain desired data from the devices.

For example, the WACP protocol specification defines five standard constructs for messaging. If a selected object supports the message in the definition, the particular messaging construct(s) are displayed on the interface 500. If a stream of data is supported, the device 102, 104, 106 will send the data at regular intervals without the monitor device 110 having to request the data.

In a more complex example, if the device 102, 104, 106 does not support streaming, the user will select a series of messages and an interval that the monitor device 110 will use to poll the device 102, 104, 106. The messaging section allows the user to build a sequence of messages allowing for dialog control with the device 102, 104, 106. This information is saved in the skin as well.

Figure 13:
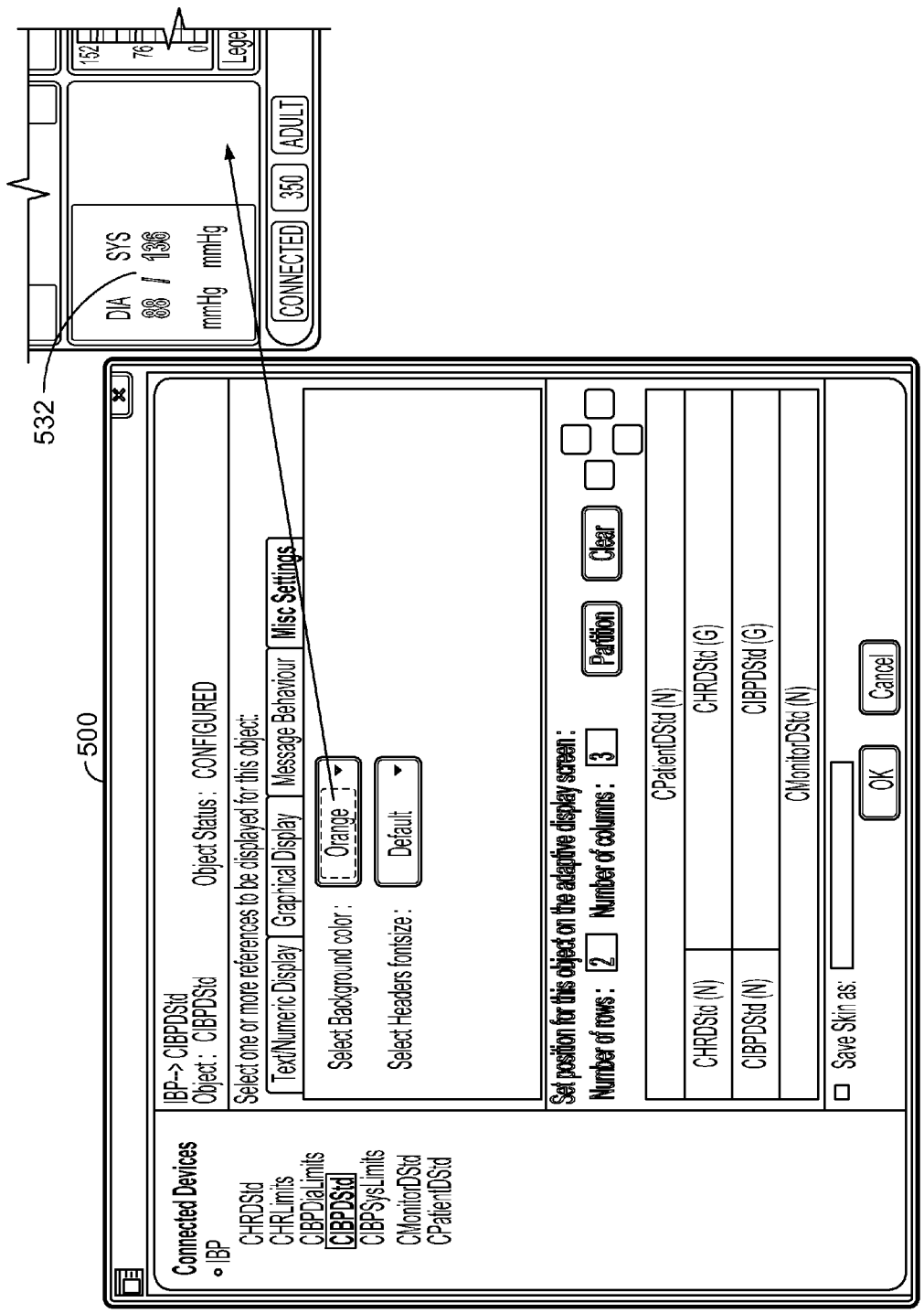
FIG. 13 shows another view of the user interface of FIG. 10.

In FIG. 13, miscellaneous options for the skin are provided when the "Misc Settings" tab is selected. Options like the background color and header font sizes can be defined, as illustrated in an example snippet 532 of the main screen region.

Figure 14:
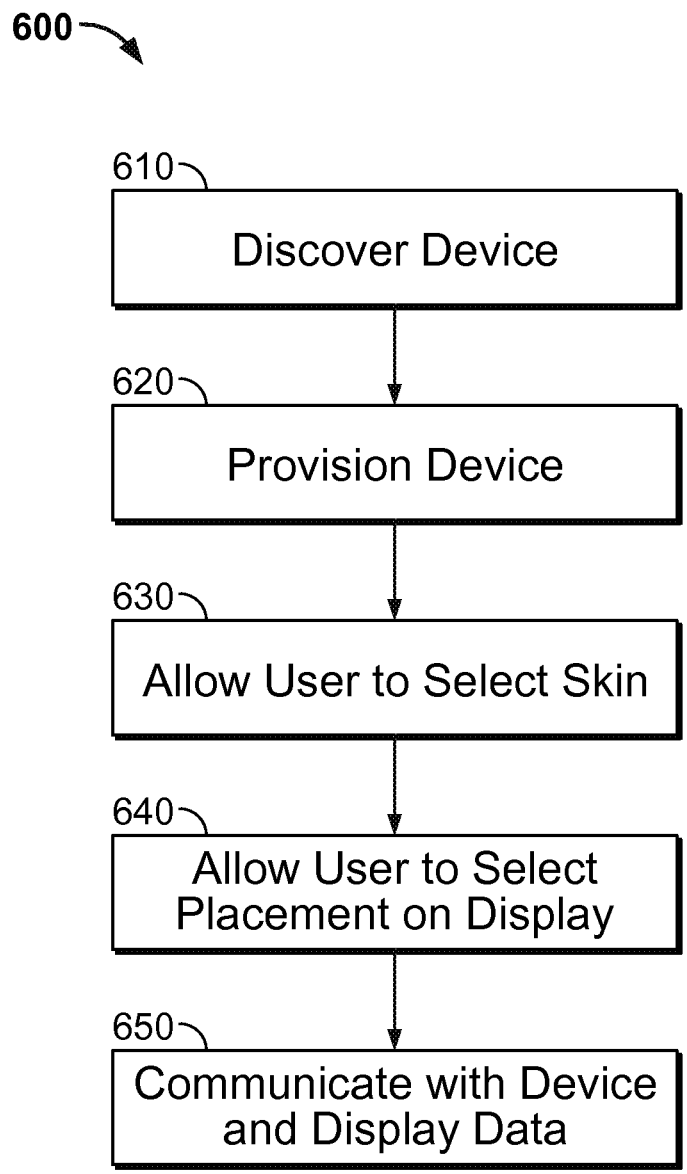
FIG. 14 shows an example method for connecting to and displaying data from a device on a monitor device.

Referring now to FIG. 14, an example method 600 for connecting and displaying data from a device on a monitor device is shown.

Initially, at operation 610, the monitor device discovers a new device that is connectable. As noted above, this discovery could happed wirelessly (e.g., a device comes within range of the monitor device) or through a wired connection.

Next, at operation 620, the monitor device provisions the device. This operation includes identifying the appropriate device data sheet(s) and any available skins for the device type. If no device data sheet and/or skin are available on the monitor device, the monitor device can connect to a server to download the necessary information.

Next, at operation 630, the user is allowed to select a skin for use in displaying the data from the device. This includes allowing the user to browse the available skins as well as to manipulate and define new skins, if desired.

Next, at operation 640, the user is allowed to select the placement of the skin on the display. In some examples, this can include dragging and dropping the skin at the desired cell of the matrix defined on the display. In addition, the user can merge cells to create a larger space for display, if desired.

Finally, at operation 650, the monitor device communicates with the device to display data on the display according to the selected skin. The data can be streamed from the device to the monitor device for display, or the monitor device can interactively prompt the device for the data. Other configurations are possible.

The various embodiments described above are provided by way of illustration only and should not be construed as limiting. Those skilled in the art will readily recognize various modifications and changes that may be made without following the example embodiments and applications illustrated and described herein, and without departing from the true spirit and scope of the disclosure.

What is claimed is:

1. A system for displaying physiological parameters, the system comprising:
   a central processing unit (CPU) that is configured to control operation of a monitor device;
   a display screen; and
   a set of one or more computer readable data storage media storing software instructions that, when executed by the CPU, cause the monitor device to:
   detect a device that is added to the system, the device being used to measure at least one physiological parameter associated with a patient;
   provision the device;
   allow a user to select a skin defining a layout for displaying data associated with the physiological parameter measured by the device;
   allow the user to select a position of a window displaying the skin, the position selected from one of a plurality of cells on a matrix displayed on the display screen;
   allow the user to define whether the data associated with the physiological parameter is displayed as text or a graph; and
   display the window on the display screen at the position.

2. The system of claim 1, wherein the CPU further causes the monitor device to allow the user to merge two or more cells to create an enhanced cell of a larger size to view the window.

3. The system of claim 1, wherein the CPU further causes the monitor device to allow the user to move the window to a different position in the matrix displayed on the display screen.

4. The system of claim 1, wherein the CPU further causes the monitor device to allow the user to modify the skin.

5. The system of claim 4, wherein the CPU further causes the monitor device to allow the user to create a new skin defining the layout for displaying the data associated with the physiological parameter measured by the device.

6. The system of claim 5, wherein the CPU further causes the monitor device to allow the user to select one or more objects associated with the data to be displayed or hidden by the new skin.

7. The system of claim 1, further comprising the device being used to measure the physiological parameter associated with the patient.

8. The system of claim 7, wherein the device is configured to measure one or more of blood pressure, pulse rate, oxygen saturation, and temperature of the patient.

9. The system of claim 1, wherein the CPU further causes the monitor device to create a second window displaying at least one physiological parameter associated with a second patient, the second window at a second position selected from the plurality of cells on the matrix displayed on the display screen.

10. The system of claim 9, wherein the CPU further causes the monitor device to:
    allow the user to select a second skin; and
    allow the user to move the second window to a second different position in the matrix displayed on the display screen.

11. A monitor device including a central processing unit (CPU) and at least one computer readable data storage medium storing software instructions that, when executed by the CPU, cause the monitor device to generate a user interface comprising:
    a matrix defined on a display of the monitor device, the matrix including a plurality of cells, each of the cells being configured to display a window displaying aspects of a physiological parameter measured by a sensor device associated with a patient, the matrix displaying at least two windows for two different patients, wherein a user is allowed to merge two or more cells of the matrix to create an enhanced cell of a larger size to view one of the windows; and
    a skin selection module displaying a plurality of skins, each of the skins defining a layout for displaying data associated with the physiological parameter measured by the sensor device.

12. The device of claim 11, wherein the user interface allows the user to move the windows to different positions in the matrix.

13. The device of claim 11, wherein the user interface allows the user to modify one or more of the skins.

14. The device of claim 13, wherein the user interface allows the user to select one or more objects associated with the data to be displayed or hidden by one of the skins.

15. The device of claim 11, wherein the physiological parameter measured by the sensor device is one or more of blood pressure, pulse rate, oxygen saturation, and temperature of the patients.

16. A method for displaying physiological parameters on a monitor device, the method comprising:
    detecting a device that is added, the device being used to measure at least one physiological parameter associated with a patient;
    allowing a user to select the device from a plurality of devices that are connected to the monitor device, wherein each of the plurality of devices includes an indicator signifying whether or not information from that device can be displayed;
    allowing the user to select a skin defining a layout for displaying data associated with the physiological parameter measured by the device;
    allowing the user to select a position of a window displaying the skin, the position selected from one of a plurality of cells on a matrix displayed on a display screen; and
    displaying the window on the display screen at the position.

17. The method of claim 16, further comprising allowing the user to merge two or more cells to create an enhanced cell of a larger size to view the window.

18. The method of claim 16, further comprising allowing the user to move the window to a different position in the matrix displayed on the display screen.

* * * * *